United States Patent [19]

Atwood et al.

[11] 4,275,592
[45] Jun. 30, 1981

[54] EXTRACTOR TOOL AND HOLDER

[75] Inventors: John E. Atwood; John L. Baugh; William M. Koehler; David K. Waterman, all of Houston, Tex.

[73] Assignee: McMurry-Hughes, Inc., Huntsville, Tex.

[21] Appl. No.: 1,224

[22] Filed: Jan. 5, 1979

[51] Int. Cl.³ ............................................. G01N 17/00
[52] U.S. Cl. ................................... 73/432 R; 73/86; 29/426.1
[58] Field of Search ............... 29/427, 700, 213 R, 29/156.7, 157.1, 213; 138/107, 108, 18; 137/315, 15, 327, 318; 73/86, 432 R

[56] References Cited

U.S. PATENT DOCUMENTS

| | | | |
|---|---|---|---|
| 2,746,470 | 5/1956 | Laird | 137/15 |
| 2,870,629 | 1/1959 | Willis | 29/213 X |
| 3,007,340 | 11/1961 | Kroftson | 73/86 X |
| 3,046,645 | 7/1962 | Smith | 29/213 X |
| 3,229,711 | 1/1966 | Leopold, Jr. et al. | 137/318 |
| 3,865,129 | 2/1975 | Peterson | 137/318 X |
| 4,002,059 | 1/1977 | Jeffers et al. | 73/86 |

Primary Examiner—Milton S. Mehr

Attorney, Agent, or Firm—Browning, Bushman & Zamecki

[57] ABSTRACT

Disclosed is a holder which may be used for mounting equipment, such as sensing apparatus, within an otherwise closed environment, and an extractor tool for inserting and retrieving the holder and attached equipment. In an operating configuration the holder is double-sealed to a landing nipple mounted on the container against communication of high pressure fluid out of the container. With the extractor tool mounted and sealed on the landing nipple also, a placement member within the extractor tool may engage the top of the holder to extract the holder from sealing engagement with the landing nipple. Two independent gear boxes are provided whereby translational and rotational motions may be separately imparted to the placement member. The holder is anchored to the landing nipple by threaded engagement between the landing nipple and a drive screw section of the holder. A separate seal section of the holder is rotated during the insertion procedure until a preselected orientation of the seal section is achieved. With the orientation of the seal section fixed, further insertion of the holder into the landing nipple without rotation of the seal section effects a metal-to-metal seal, in addition to a packing-type seal, between the seal section and the landing nipple.

59 Claims, 11 Drawing Figures

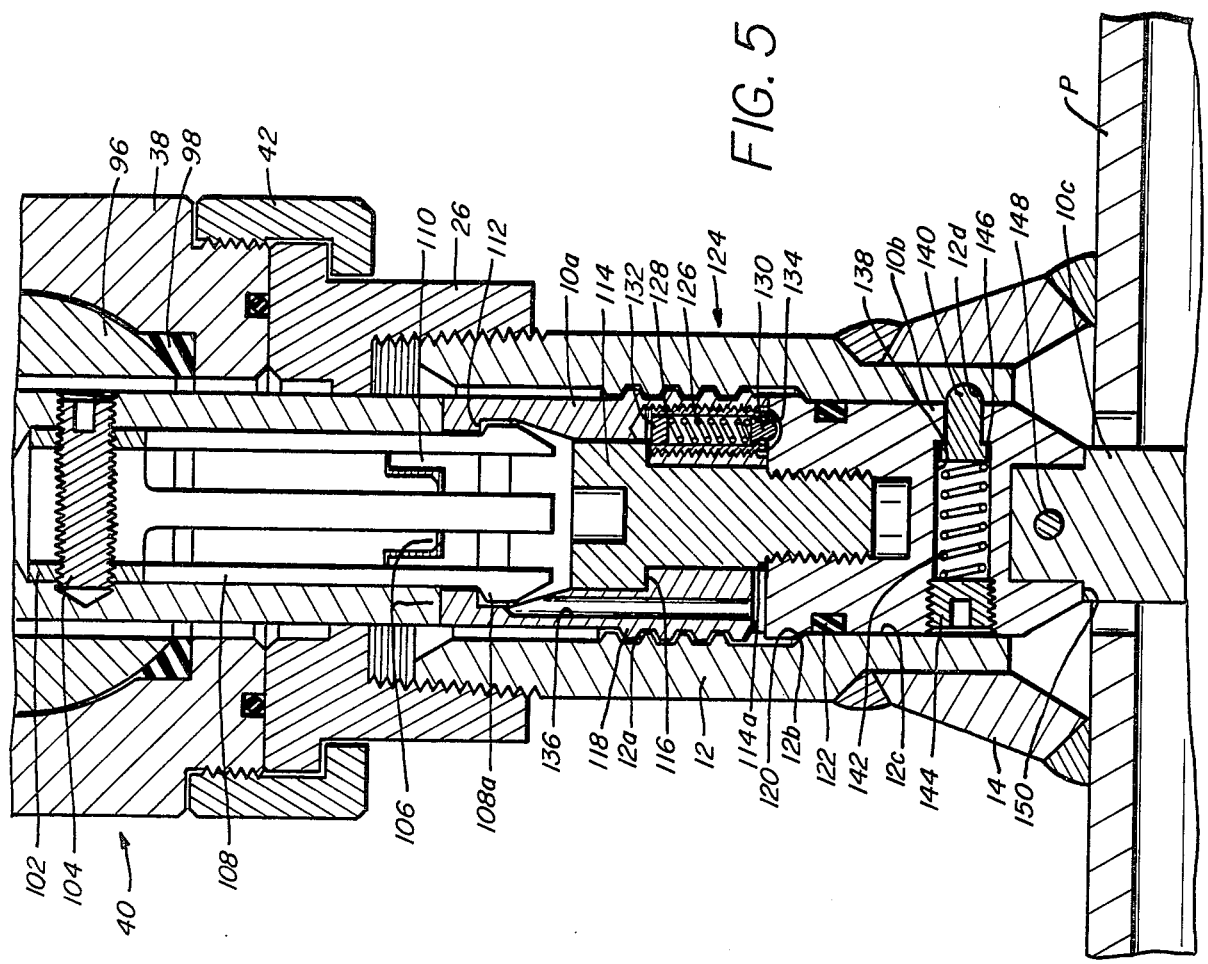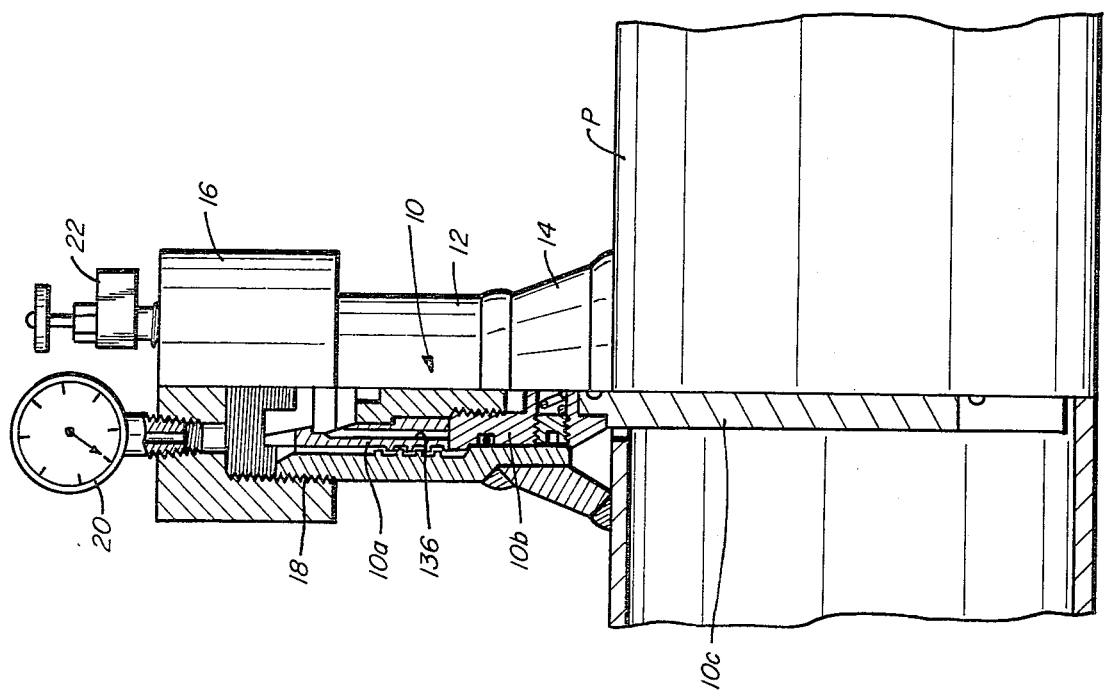

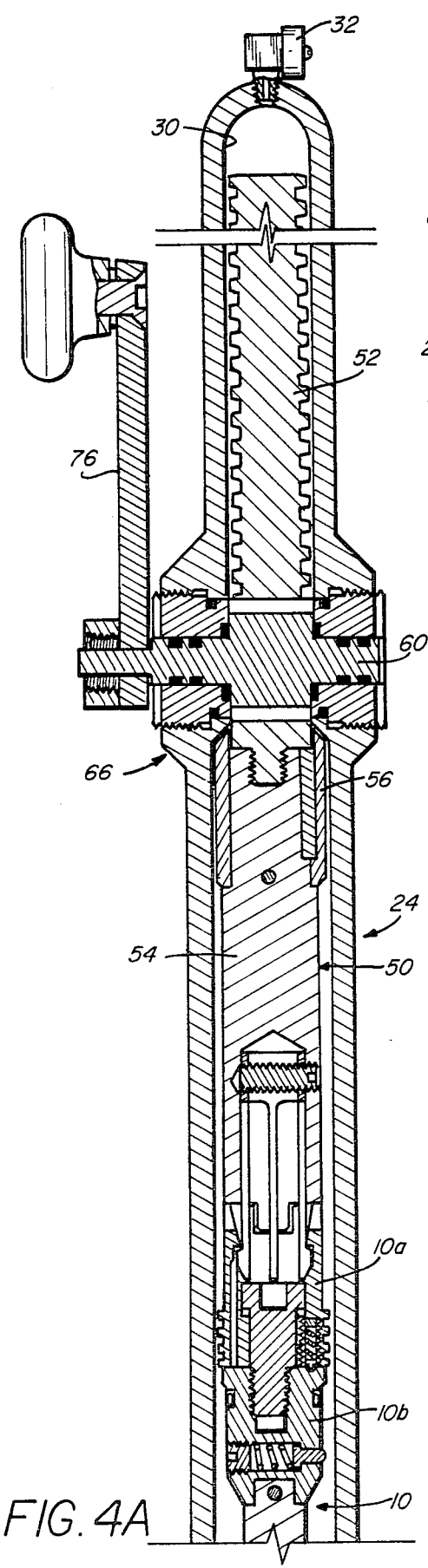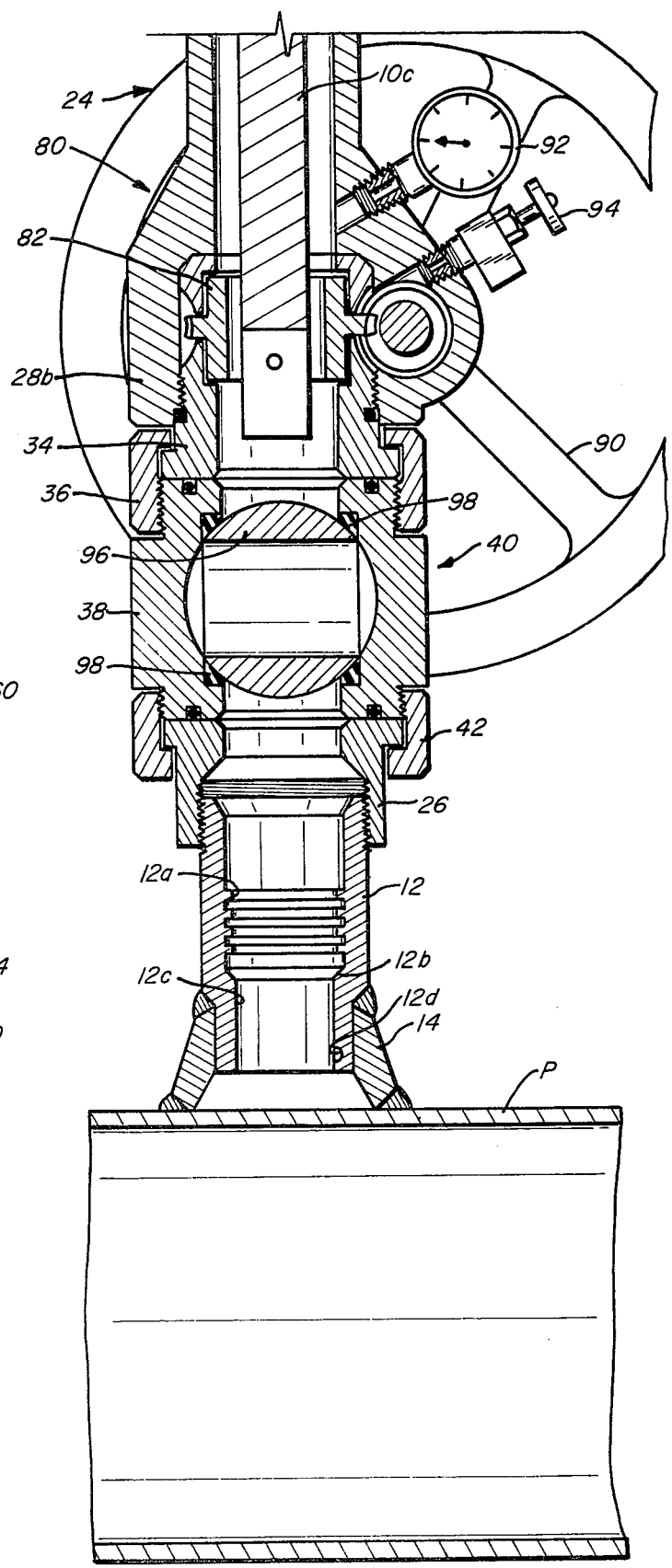
*FIG. 4A*  *FIG. 4B*

EXTRACTOR TOOL AND HOLDER

BACKGROUND OF THE INVENTION

1. Field of the Invention

The present invention pertains to apparatus for gaining access to the interior of containers. More particularly, the present invention is related to holders for mounting equipment such as sensing or measuring devices within high pressure containers, and tools for inserting and retrieving such holders without exposing the interior of the container to the surrounding atmosphere. Such apparatus is particularly applicable to high pressure fluid pipelines whereby sensors, such as corrosion or scale testing coupons, may be inserted into the fluid flow and retrieved therefrom without shutting down the pipeline flow.

2. Description of Prior Art

In various industrial settings, it is often necessary to test or sample material under pressure in a pipeline or other enclosure. Access to such material may conceivably be had by first relieving the pressure, or shutting down the flow in the pipeline. This may be a difficult or dangerous procedure, and will usually be expensive. Retrieval tools, or retractors, are known for inserting holders or other fittings through a hole, for example, in the side of a pipe member without the need for shutting down the high pressure pipeline flow. The retrieval tools are also used to withdraw the holders from the pipeline without losing pipeline pressure.

While the holder is in position extending into the interior of the pipeline, a seal is maintained between a fitting mounted on the pipeline and the holder, or equipment attached thereto. During the removal of the holder from the pipeline, continuous sealing to maintain the pipeline pressure must be carried out. The holder must be capable of being totally withdrawn from the pipeline to allow access to testing equipment mounted on the holder for insertion within the pipeline. Thus, the fitting secured to the pipeline must be provided with a valve or other closure device to seal off the pipeline in the absence of the holder.

According to some prior art practices, a valve such as a gate valve is permanently installed on a fitting attached to the pipeline to selectively open and close communication to the tap hole in the side of the pipe. To install a holder extending into the pipeline a retrieval tool is secured and sealed to the valve housing with the holder positioned within the retrieval tool. The valve is opened and the retrieval tool is operated to advance the holder through the valve passage toward the pipeline. The procedure is generally reversed to retrieve the holder from the pipeline.

One type of retrieval tool must remain sealed to the valve housing as long as the holder is in position extending into the pipeline. In such case, the integrity of the sealing of the pipeline pressure is maintained by seal members carried by the retrieval tool rather than the holder.

In another type of tool, the holder may be sealed to fittings attached to the pipeline, and the retrieval tool removed. However, movement of the holder toward or away from the pipeline in the latter case is effected by moving a rod, to which the holder is attached, through a packing gland. A pressure differential across the packing gland may result in unintended movement of the rod.

Advancement of the holder according to prior art apparatus is generally achieved by rotating a screw device to which the holder is attached. Such rotation precludes the use of a metal-to-metal seal between the holder and the pipeline fittings. Another disadvantage of such rotation of the holder is the difficulty in providing the exact alignment within the pipeline of the equipment mounted on the holder. For example, where material testing samples, or coupons, are being placed within a high pressure fluid flow, the effect on the testing material may be altered depending on the orientation of the coupon relative to the direction of fluid flow. Generally, where scaling effects are to be determined, the coupon which is laminar in shape is placed with a flat side perpendicular to the direction of flow. For corrosion testing, coupons are placed parallel to the flow direction. Where the holder is advanced solely by a screw action, the orientation of attached coupons will be determined by the final position of the holder relative to the pipeline fittings. Even where additional orientation adjustments to the holder and attached coupons may be made, such adjustment may be difficult and dangerous operations due to the high pressure within the pipeline. Furthermore, since the operator cannot see the coupon, he must depend on fiducial marks on the holder if exposed, or on the retrieval tool.

Another type combination retrieval tool and holder is known whereby the holder may be secured and sealed to a fitting on the pipeline without the need for a permanent valve installation. To insert or to remove the holder a valve is connected to the pipeline fitting, and the retrieval tool is sealed to the top of the valve housing. The valve is opened and the retrieval tool is operated to advance a rod through the valve passage to either insert or retrieve the holder. Again, advancement of the holder is effected by rotating the rod to which the holder is attached. Thus, as discussed hereinbefore, a metal-to-metal seal between the holder and the pipeline fitting is precluded. Also, the holder and attached coupons must be oriented after the holder is sealed to the pipeline fitting. In this particular type of tool, rotation of the rod to advance or retract the holder is effected by turning an exterior sleeve of the tool.

Gaining access to the interior of a high pressure pipeline may be dangerous, particularly where such procedure is carried out manually. Consequently, it is highly desirable that retrieval tools and holders be designed to maximize safety and ease of use. For example, in the case of a blowout during operations with the retrieval tool, it may be expected that the major thrust of the escaping pressurized fluid will be along the pipeline fitting perpendicular to the pipeline itself. Thus, it is preferred that the retrieval tool be operable without the need for the operator to be positioned above the retrieval tool, in line with the possible blowout thrust. Further, the tool should be light weight and require no awkward or difficult movements by the operator in, for example, effecting rotation of an internal mandrel. It is also advantageous if the tool is designed for operation by one operator so that the coordination of movements by two or more individuals is unnecessary. Finally, the uncertainty of the orientation of the equipment positioned within the pipeline may be removed by a holder which is automatically oriented as desired when finally positioned on the pipeline.

SUMMARY OF THE INVENTION

The present invention provides an extractor or manipulating tool and a holder which permits the holder to be secured and sealed directly to a landing nipple attached to, for example, a high pressure pipeline. The extractor tool incorporates a valve through which the holder may be passed in either a retrieval or insertion operation. During retrieval, the holder may be withdrawn clear of the valve, and the extractor tool broken above the closed valve to allow access to the holder. The extractor tool may then be reassembled, the valve opened, and the holder returned through the valve to the pipeline.

The holder is advanced or retracted by operation of a placement member within the extractor tool. Generally, translational movement and rotational movement may be imparted to the placement member independently by means of two gear boxes at the disposal of the operator. The placement member includes a cylindrical rack engaged to a spur gear in the first gear box for producing translational movement. A spline collar located along the placement member engages a worm gear at the second gear box when the placement member is positioned generally toward the pipeline. Thus, the placement member may be moved translationally without rotation thereof, and, with the spline collar engaging the worm gear, the placement member may be rotated about its longitudinal axis unaccompanied by translational movement.

The placement member includes a torque head which may engage the holder and impart both translational as well as rotational movement to the holder. Engagement between the torque head and the holder is effected or broken generally by relative translational motion between the torque head and the holder.

The holder includes a drive screw which serves to anchor the holder to the landing nipple attached to the pipeline, and a seal section which provides the sealing engagement between the holder and the landing nipple. A holder section, on which equipment such as coupons may be mounted, is connected to the seal section.

The drive screw is joined to the seal section by a shoulder bolt which permits limited relative translational movement between the drive screw and the seal section, but allows rotational movement therebetween. A clutch is provided to lock the drive screw against rotational movement relative to the seal section. The seal section and/or the attached holder section is equipped with an anchoring or orientation device which engages the landing nipple when the seal section is positioned therein and oriented in a predetermined direction. The anchoring of the seal section against rotation relative to the landing nipple occurs automatically, and thus assures the preferred orientation of equipment attached to the holder. In two embodiments disclosed, the seal section orientation device operates by spring-biasing to engage a detent, or recess, in the interior wall of the landing nipple.

The landing nipple provides an annular, longitudinally extending sealing surface to receive a packing-type seal carried by the seal section. A second seal is provided by contact between complimentary frustoconical surfaces on the landing nipple and the seal section.

The drive screw is anchored to the landing nipple by matching low pitch threads. As the drive screw is being rotated by means of the extractor tool to anchor the holder to the landing nipple, the clutch causes the seal section to rotate with the drive screw. When the seal section has been advanced sufficiently in the area of the landing nipple sealing surfaces, the seal section anchor device engages the detent or recess of the landing nipple and the clutch is overridden as the drive screw is further rotated. Thereafter, advancement of the drive screw along the landing nipple threads occurs with rotation of the drive screw but without further rotation of the seal section. The aforementioned metal-to-metal seal provided by the frustoconical surfaces of the landing nipple and the seal section is closed by the drive screw being tightened on the seal section by means of the landing nipple threads.

During the retrieval process the drive screw is slowly raised by rotation along the landing nipple threads and the seal section is gradually lifted by the drive screw to provide a slow, controlled disengagement of the seals between the seal section and the landing nipple.

Except when the drive screw is being engaged or disengaged with the threads of the landing nipple, the placement member may be moved along the extractor tool housing, with or without the holder attached, by operation of the first gear box to impart translational movement only. The second gear box is used to rotate the placement member with the holder attached for such engagement and disengagement between the drive screw and the landing nipple. Only when the placement member is engaged with the holder, and the drive screw thereof is threadedly engaged with the landing nipple will operation of the second gear box to rotate the placement member result in translational movement thereof as well.

As the holder is being moved toward the landing nipple in an insertion procedure, the second gear box may be operated to rotate the placement member and holder prior to contact between the drive screw and the landing nipple threads. Then, once the threads of the drive screw contact the threads of the landing nipple due to the translational movement imparted to the holder by means of the first gear box, the threads will mesh and the rotation of the drive screw will effect a longitudinal pull on the placement member. This translational pull may be detected by the resulting torque on the handle by which the first gear box is operated. Thus, the operator will know when the threads of the drive screw have contacted those of the landing nipple.

The present invention provides equipment for access to high pressure pipelines which is capable of operation by a single operator without the need for the operator being positioned in line with the extractor tool. Further, the extractor tool carries its own valve, and may be removed from the landing nipple attached to a pipeline after the holder is secured and sealed to the landing nipple. In addition to a packing seal, the holder effects a metal-to-metal seal to the landing nipple, which seal is effectively closed without rotation of the seal section relative to the landing nipple. The holder includes an automatic orienting device which assures the desired orientation of the holder and attached equipment relative to the fluid flow direction within the pipeline. The gear boxes may be operated by simple crank handles which are easy to use by a sole operator. The extractor tool itself may be of light weight construction for additional ease of operation. Further, by appropriate choice of seal materials within the extractor tool as well as the holder and landing nipple, apparatus according to the present invention may be utilized on high pressure pipelines carrying fluid of extreme temperature, either high or low.

BRIEF DESCRIPTION OF THE DRAWINGS

FIG. 1 is a side elevation in quarter section of a coupon holder according to the present invention, extending in operating position within a pipe;

FIGS. 4A and 4B together are side elevations in cross section similar to FIGS. 3A and 3B together, with the placement member of the tool and the coupon holder raised above the ball valve;

FIG. 5 is an enlarged elevation in cross section of a segment of the extractor tool showing the placement member engaged with the coupon holder, and the pressure equalization port through the drive screw of the coupon holder open;

DESCRIPTION OF PREFERRED EMBODIMENTS

Figures 2A, 2B:
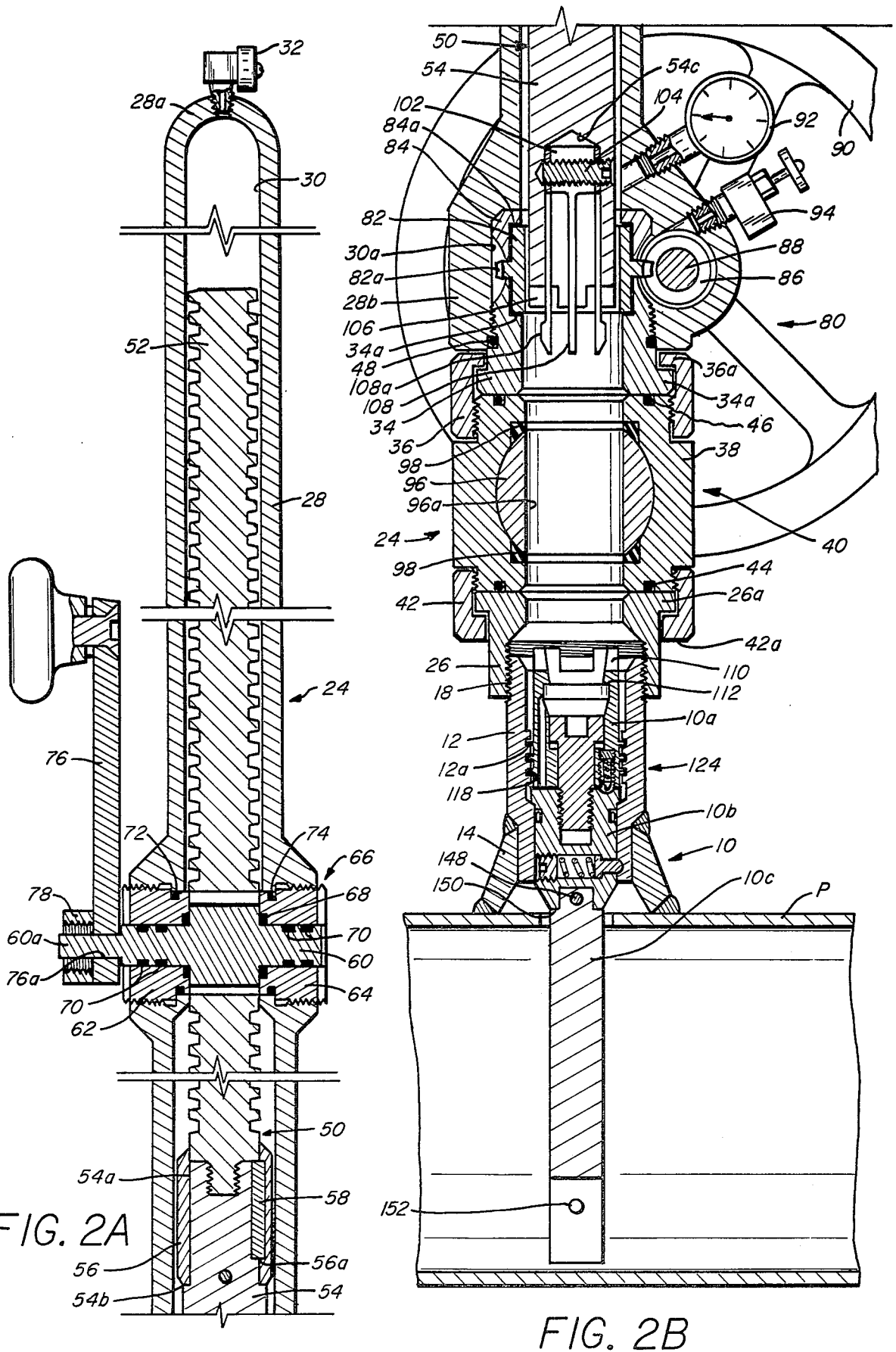
FIGS. 2A and 2B together comprise a side elevation in cross section of an extractor tool according to the present invention joined to the landing nipple securing the coupon holder of FIG. 1 to the pipe, with FIG. 2A showing the top of the tool and FIG. 2B showing the bottom.

In FIG. 1, a coupon holder according to the present invention, shown generally at 10, is secured in operating position, extending through a tap hole in a pipe member P, by means of a landing nipple 12. While the landing nipple may be designed to be fixed directly to the pipe member P, the nipple is shown welded to a flared base 14 which is welded directly to the pipe. The coupon holder at 10 includes three general sections: a drive screw 10a; a seal section 10b; and a holder section 10c. The drive screw 10a fixes the coupon holder to the landing nipple 12 against longitudinal movement relative thereto. The seal section 10b seals the coupon holder to the landing nipple 12 and, therefore, to the pipe P. The construction and function of the various sections of the holder 10 are discussed in detail hereinafter.

With the holder 10 positioned and secured within the landing nipple 12, a cap 16 may be used to close the exterior open end of the nipple. The cap 16 is threadedly engaged to the landing nipple by external nipple threads 18 which also serve a purpose discussed hereinafter. Thus, the cap 16 not only covers the top of the holder 10, but also protects the aforementioned threads 18. A pressure gauge 20 and a bleed valve 22 are secured sealed to the cap and communicate with the interior thereof. The pressure gauge 20 may be used to detect any pressure buildup above the seal section 10b due to leakage of high pressure fluid from within the pipe P by the seal section. In case of such a pressure buildup, the bleed valve 22 may be opened to allow the fluid pressure to leak to the atmosphere before the cap 16 is removed from the landing nipple 12. Thus, a dangerous situation inherent in an attempt to remove the cap 16 in the presence of such a pressure buildup above the seal section 10b may be avoided.

In FIGS. 2A and 2B, the cap 16 has been replaced by an extractor tool, shown generally at 24, according to the present invention. A floating nut 26 threadedly engages the landing nipple 12 by way of the external nipple threads 18 whereby the extractor tool 24 is secured to the pipe P.

The tool 24 includes an elongate housing 28 defining an inner chamber 30 that extends the length of the housing. One end of the housing 28a is closed except for a bleed valve 32 which may be used to selectively open a leak path to the environment. The opposite end of the housing 28b is enlarged in transverse dimension to include a portion of the inner chamber 30a of increased transverse dimension compared to the remainder of the chamber 30.

A worm gear retainer 34 extends into the enlarged chamber area 30a and threadedly engages the end of the housing 28b. The end of the worm gear retainer 34 external to the housing 28 features a radially outwardly extending flange 34a which is overlapped by a radially inwardly extending flange 36a of a nut 36. The nut 36 threadedly engages the housing 38 of a ball valve shown generally at 40. Similarly, the upper end of the floating nut 26 features a radially outwardly extending flange 26a which is overlapped by a radially inwardly extending flange 42a of a nut 42. The latter nut 42 threadedly engages the ball valve housing 38.

With the nuts 36 and 42 tightened on the valve housing 38, the worm gear retainer 34 and the floating nut 26, respectively, are held fixed relatively to the valve housing 38. Therefore, with the threaded engagement between the worm gear retainer 34 and the housing 28 tightened, the entire extractor tool is secured to the landing nipple, and, therefore, to the pipe P. O-ring seals 44 and 46 fluid-seal the floating nut 26 and the worm gear retainer 34, respectively, to the valve housing 38. An O-ring seal 48 fluid-seals the worm gear retainer 34 to the housing 28. As in the case of the cap 16, the floating nut 26 may be sufficiently tightened on the threads 18 of the landing nipple 12 to effect a fluid-tight engagement therebetween. Thus, with the cooperation of additional sealing described hereinafter, the inner chamber 30 may communicate with the interior of the landing nipple 12 by way of the ball valve at 40, without fluid communication to the environment surrounding the extractor tool 24 and the pipe P.

A placement member, shown generally at 50, is positioned within the housing 28 for movement along the chamber 30. The placement member 50 includes a cylindrical rack 52 and a torque head 54. While the rack 52 and the torque head 54 may be of generally unitary construction, they are shown as two elements joined together by a threaded connection. A spline collar 56 is received over a section 54a of reduced diameter of the torque head 54 at the threaded junction with the rack 52, and is locked against rotational movement relative to the torque head by a key 58 received in appropriate grooves in both the torque head and the spline collar. The key 58 is held against longitudinal movement by the base of the rack 52 joined to the torque head. The spline collar 56 is then held against upward and downward longitudinal movement relative to the torque head 54 by a shoulder 56a marking the end of the spline collar groove receiving the key 58, and an annular shoulder 54b marking the end of the reduced diameter section 54a of the torque head, respectively. Thus, with the rack 52 joined to the torque head 54 as shown, the spline collar 56 is fixed against rotational and longitudinal movement relative to both the rack and the torque head.

Figure 6:
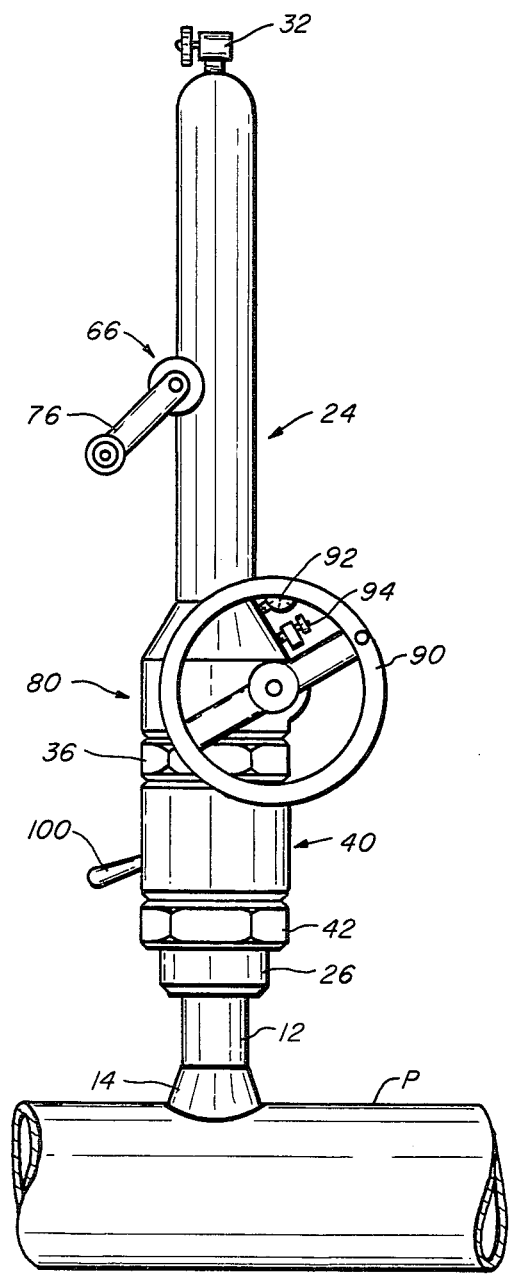
FIG. 6 is a side elevation of the extractor tool secured to a pipe, arranged with both crank handles on the same side.
Figure 7:
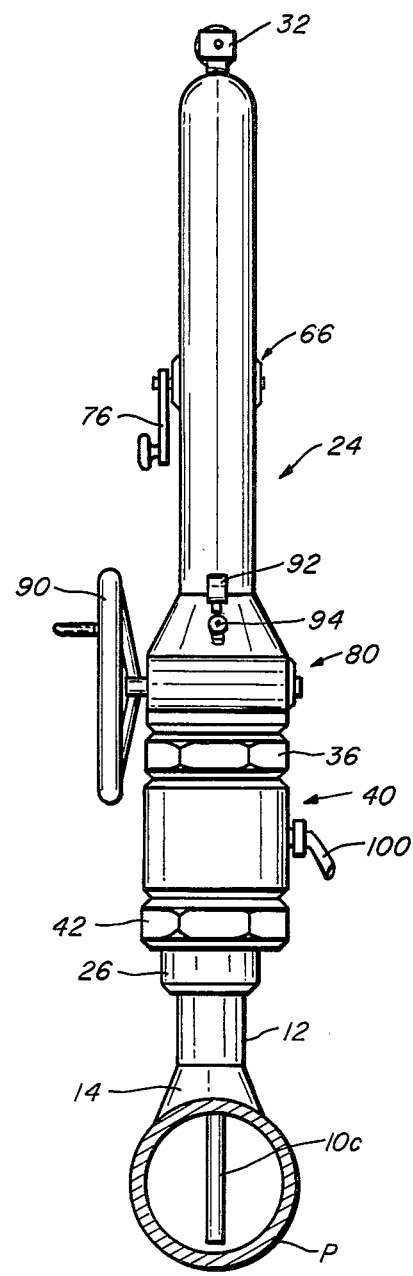
FIG. 7 is an end elevation of the extractor tool of FIG. 6 secured to a pipe.

The placement member may be selectively moved along the inner chamber 30 by rotation of a spur gear 60 with which the cylindrical rack 52 is meshed. The spur gear 60 is positioned between two gear retainers 62 and 64 which are joined by threaded connection to the housing 28 at an enlarged offset portion thereof to form a first gear box indicated generally at 66. The spur gear 60 rides on thrust bearings 68 positioned in annular grooves in both gear retainers 62 and 64. O-ring seals 70 are provided to fluid-seal the shaft of the spur gear to both gear retainers. O-rings 72 and 74 further seal the retainers 62 and 64, respectively, to the housing 28. One end of the spur gear shaft 60a carries a crank handle 76 held to the shaft by a nut 78. The extended spur gear shaft portion 60a is arcuate in cross section and is received through a matching arcuate hole 76a in the handle 76 to lock the handle against rotational movement relative to the spur gear 60. The position of the first gear box 66 relative to the housing 28 may be further appreciated by reference to FIGS. 6 and 7.

A second gear box, indicated generally at 80, is formed at the enlarged end of the housing 28b. A worm gear 82 rides on a radially inwardly extending shoulder 34a of the worm gear retainer 34. A collar 84 is equipped with a radially inwardly extending flange 84a to further prevent longitudinal movement of the worm gear 82 along the enlarged chamber area 30a.

The worm gear 82 features a ring of radially outwardly extending teeth 82a which mesh with a helical gear 86 carried on a shaft 88. The helical gear 86 and shaft 88 are positioned in an appropriate throughbore in the wall of the enlarged housing end 28b. A second crank handle in the form of a wheel 90 is fixed to the shaft 88 to control rotational movement thereof. Then, rotation of the wheel 90 causes rotation of the helical gear 86 which is fixed against rotation relative to the shaft 88.

Both the collar 84 and the gear retainer 34 are tapered toward the worm gear 82 as shown to accommodate the helical gear 86 and the shaft 88. However, both tapered ends of elements 34 and 84 may contact the worm gear 82 at the teeth 82a to provide additional support for the worm gear.

As the helical gear is rotated, interaction between this gear and the teeth 82a of the worm gear causes rotation of the worm gear 82 about its axis of cylindrical symmetry, which is essentially coincidental with the longitudinal axis of the inner chamber 30. The interior of the worm gear 82 features a plurality of radially inwardly extending splines which mesh with an equal number of radially outwardly extending splines on the spline collar 56. However, such engagement between the worm gear 82 and the spline collar 56 occurs only when the placement member at 50 is positioned along the inner chamber 30 so that the spline collar overlaps the worm gear. This is the case in FIGS. 3A and 3B wherein the placement member 50 is shown in a lowered position and engaging the coupon holder at 10.

It will be appreciated that engagement of the spur gear 60 with the rack 52 may be used to provide translational movement of the placement member 50 along the inner chamber 30, while engagement of the worm gear 82 with the spline collar 56 may be used to provide rotational motion of the placement member about its longitudinal axis. However, such engagement between the spur gear 60 and the rack 52 does not prevent the placement member 50 from being rotated. Similarly, such engagement between the worm gear 82 and the spline collar 56 does not prevent translational movement of the placement member along the inner chamber 30.

A pressure gauge 92 and a bleed valve 94 are secured to the wall of the enlarged housing end 28b, and communicate, by way of appropriate passages therethrough, to the interior of the housing 28. As in the case of the gauge 20 and valve 22 fixed to the cap 16, the gauge 92 and the valves 94 and 32 are tightened in their respective threaded holes in the housing 28 to provide fluid-tight sealing. Similarly, the shaft 88 may ride on bearings secured, in conventional manner, by retainers (not shown) joined to the housing end 28b, and be fluid-tight sealed ultimately to the housing at 28b. Thus, the integrity of the fluid-tight sealing of the inner chamber 30 is preserved by the seals and fittings provided at the first gear box 66 as well as the second gear box 80.

The ball valve at 40 includes a valve element 96 with a central passage 96a of approximately the same diameter as that of the inner chamber 30. Appropriate packing rings 98 are provided to seal the valve element 96 to the valve housing 38. The valve 40 may be selectively opened or closed, as in FIG. 4B, by operation of a handle 100 shown in FIGS. 6 and 7. The handle 100 is fixed to a shaft (not shown) extending through the housing 38 and engaging the valve element 96 in conventional fashion.

Figures 3A, 3B:
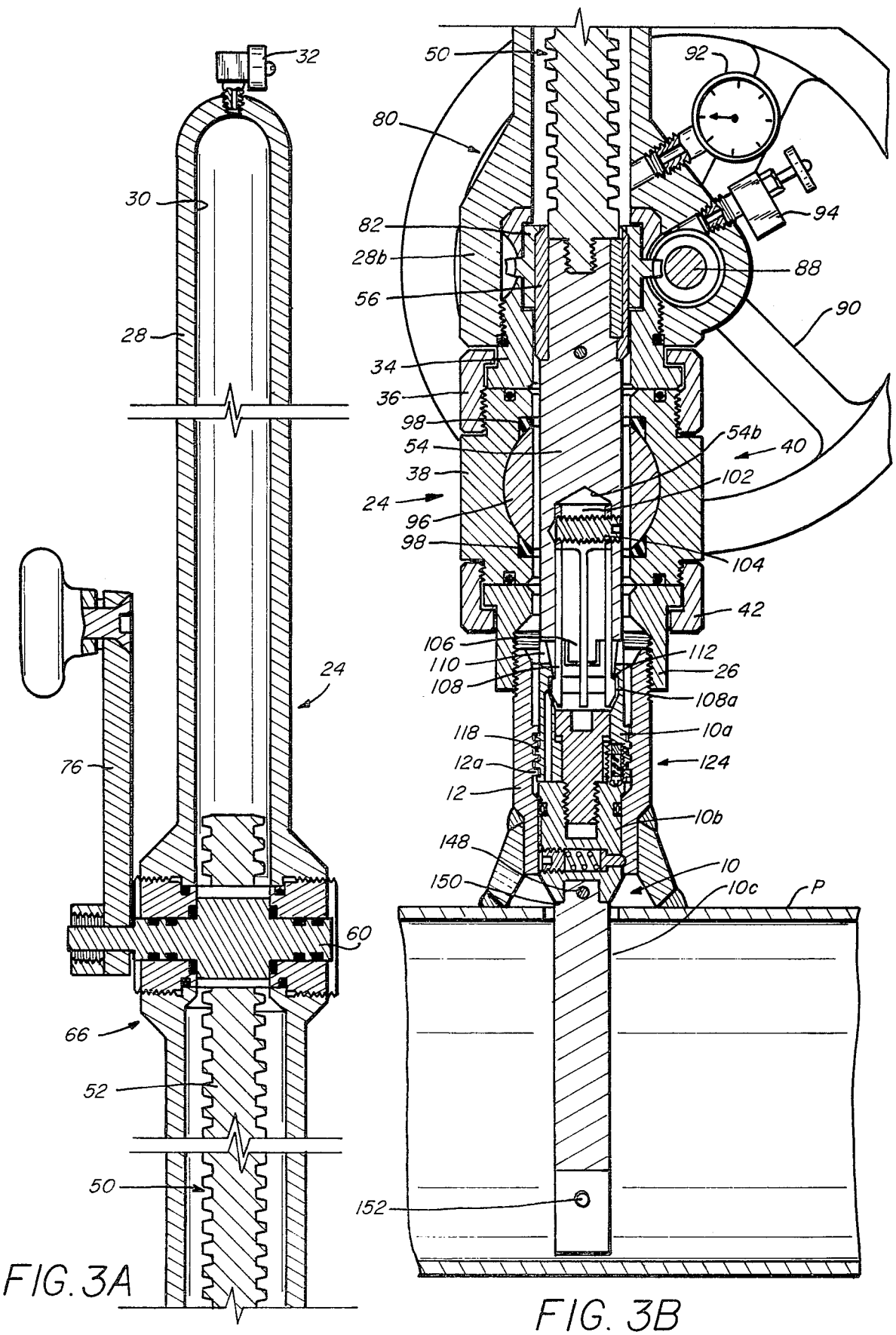
FIGS. 3A and 3B together are side elevations in cross section similar to FIGS. 2A and 2B together, with the placement member of the tool engaging the coupon holder.

The worm gear retainer 34, the ball valve housing 38, and the floating nut 26 also provide interior passages therethrough corresponding in cross section to the inner chamber 30. Thus, the placement member 50 may be moved through the valve, in open configuration, and out through the floating nut 26. Only the spline collar 56 is closely confined against lateral movement upon engagement with the worm gear 82. Thus, rotation of the spur gear 60 in the appropriate rotational sense may be used to lower the placement member 50 to engage the holder 10 as shown in FIGS. 3A and 3B.

The lower end of the torque head 54 features an upwardly extending recess 54c. A collet assembly 102 is positioned within the recess 54c and held therein by a set screw 104 secured within an appropriate threaded hole in the side of the torque head 54.

As may be seen in FIG. 2B, the end of the torque head 54 is scalloped to form a plurality of downwardly extending projections, or rotary drive dogs, 106. A plurality of collet fingers 108 of the assembly 102 extend downwardly beyond the rotary drive dogs 106, and end in radially outwardly facing latches 108a. The collet fingers are formed biased radially outwardly.

The drive screw 10a of the holder 10 is generally tubular in construction. The top end of the drive screw 10a is scalloped in the manner of the bottom end of the torque head 54, and features a like number of upwardly extending projections, or rotary drive dogs, 110. An undercut shoulder 112 is formed within the drive screw 10a just below the dogs 110. The placement member 50 thus engages the holder 10 by the collet fingers 108 extending down within the drive screw 10a so that the latches 108a catch behind the undercut shoulder 112, and the rotary drive dogs 106 of the torque head 54 mesh with the matching dogs 110 of the drive screw, as seen in FIG. 3B. As long as such engagement is maintained, the drive screw 10a is fixed relative to the placement member 50 against both rotational as well as translational movement.

Details of the coupon holder 10 as well as its engagement with the placement member 50 may be further appreciated by reference to FIG. 5. The drive screw 10a is connected to the seal section 10b by means of a shoulder bolt 114 whose head engages a radially inwardly directed shoulder 116 of the drive screw to limit translational movement of the drive screw away from the seal section. A shoulder 114a of the bolt 114 limits the insertion of the bolt into a threaded bore in the seal section 10b by which the bolt is joined to the seal section. The shank of the bolt 114 between the head and the shoulder 114a is greater than the length of the drive screw from its bottom end of the shoulder 116. Consequently, the length of the bolt shank permits limited translational movement between the drive screw 10a and the seal section 10b.

The external surface of the drive screw is equipped with course, low pitch threads 118 which mesh with corresponding threads 12a along the interior of the landing nipple 12. The interior of the landing nipple is reduced in diameter below the threads 12a, with the change in lateral dimension of the nipple interior marked by an upwardly facing frustoconical annular shoulder 12b. The seal section 10b is topped by a radially outwardly extending flange establishing a downwardly facing frustoconical annular shoulder 120. The two shoulders 12b and 120 have complimentary angles of taper. Thus, with the drive screw 10a sufficiently advanced along the threads 12a of the landing nipple 12 to press downwardly against the seal section 10b, as illustrated in FIGS. 1, 2B and 3B, the two shoulders 12b and 120 form a metal-to-metal seal between the coupon holder and the landing nipple.

The seal section 10b carries, in an appropriate groove, resilient packing material 122 which engages the landing nipple interior surface 12c below the shoulder 12b. The surface 12c acts as a seat to receive the packing 122 to provide a primary seal between the seal section 10b and the landing nipple 12. The packing material 122 may be of any suitable composition and construction, including an O-ring.

A friction clutch, shown generally at 124, provides a further engagement between the drive screw 10a and the seal section 10b. The clutch 124 includes a spring 126 constrained within a sleeve 128 between a plunger 130 and a plug 132 closing one end of the sleeve. The opposite end of the sleeve has a diminished opening through which only the rounded face of the plunger 130 may protrude. The sleeve is threadedly anchored within a bore drilled through the bottom face of the drive screw 10a. The top face of the seal section 10b features a detent 134 which may receive the plunger 130, biased downwardly by the spring 126. With the plunger 130 engaged in the detent 134, the seal section 10b is made to rotate with the drive screw 10a unless otherwise prevented, as discussed hereinafter.

The drive screw 10a is also equipped, for a purpose described hereinafter, with one or more pressure equalization ports 136 extending longitudinally between the lower face of the drive screw and the interior thereof above the shoulder bolt 114.

A lateral throughbore 138 in the seal section 10b contains a second plunger 140 biased radially outwardly by a spring 142 which is held within the throughbore by a set screw 144. An annular shoulder 146 marking a reduced diameter portion of the throughbore 138 prevents the flanged plunger 140 from moving completely out of the seal section 10b. The landing nipple is equipped with a recess or detent 12d (see FIG. 4B) which receives the plunger 140 when the seal section 10b is in the position shown in FIGS. 1, 2B, 3B and 5. Engagement of the plunger 140 with the detent 12d constrains the seal section 10b against rotational motion relative to the landing nipple 12.

As may be better seen in FIG. 2B and FIG. 3B, the holder section 10c includes a shaft with both ends generally in the form of a flattened tab. The upper end of the shaft is received by a recess in the bottom of the seal section 10b, and anchored by a rivet or bolt 148. A shoulder 150 on the holder section 10c engages the bottom of the seal section 10b to maintain the holder section aligned with the seal section and the drive screw 10a.

The bottom tab of the holder section 10c may receive a coupon on either side thereof. A hole 152 is provided for receiving a bolt to secure the coupons to the holder section 10c. Coupons are generally flat material samples, and may readily be applied to the coupon holder 10 in this manner. With the coupons lying flat against the tab of the holder section 10c, their orientation is constrained by that of the holder section. Further, the rotational orientation of the holder section 10c is determined by that of the seal section 10b. Engagement of the spring biased plunger 140 in the landing nipple detent 12d limits the rotational orientation of the seal section 10b in operating configuration as shown in FIGS. 1, 2B and 3B to that which aligns the lower tab of the holder section 10c and, therefore, and coupons attached thereto with the longitudinal direction of the pipe P. Consequently, any coupon placed in the pipe on the holder section 10c will be oriented so that fluid flow through the pipe will be along the flat surfaces of the coupon with an edge of the coupon facing upstream. In practice, this is the generally preferred orientation for such coupons used in corrosion testing. However, it will be appreciated that any orientation of the coupon may be effected, for example, by moving the location of the landing nipple detent 12d to a different rotational position, or by changing the rotational orientation of the holder 10c relative to the seal section 10b.

Operation and use of the extractor tool and coupon holder according to the present invention may be appreciated by a consideration, with reference to FIGS. 1-7, of the procedure that may be followed in replacing a coupon being used as a test element subject to high pressure fluid flow within the pipe P.

At the start of the procedure, the coupon to be replaced, although not shown in the drawings, would be mounted on the lower tab of the holder section 10c as described hereinbefore, and the coupon holder 10 would be in operating configuration as shown in FIGS. 1 and 2B (with the cap 16 in place as in FIG. 1). In its operating configuration, the coupon holder 10 is held firmly within the nipple 12 by the drive screw 10a advanced as far as it can go along the threads 12a of the landing nipple 12. Thus, the drive screw 10a presses down against the seal section 10b, effectively closing off the pressure equalization port 136 against the top of the seal section, and maintaining surfaces 12b and 120 of the nipple 12 and seal section 10b, respectively, in fluid-sealing engagement. The primary seal is established between the packing 122 and the seating surface 12c of the nipple 12. Also, the spring biased plunger 140 sits within the nipple detent 12d.

The pressure gauge 20 may be referenced to discover the pressure within the landing nipple 12 and above the seal section 10b. A significant pressure reading would indicate leakage of fluid from the high pressure pipe P by the seal section 10b. If such high pressure exists above the seal section 10b, the bleed valve 22 may be opened to slowly leak fluid to the atmosphere to equalize the pressure on both sides of the cap 16. With the pressure so equalized, the cap 16 may be removed while the coupon holder 10 retains its dual seal with the landing nipple.

The extractor tool 24 is mounted on the landing nipple 12 by threading and tightening the floating nut 26 on the threads 18 of the landing nipple. If necessary, the nut 42 may be loosened to allow convenient rotation of the floating nut 26 to secure a fluid-tight seal to the landing nipple 12. The nut 42 may then be tightened onto the valve housing 38.

With the ball valve as shown in FIG. 2B, the first crank handle 76 is rotated in the appropriate rotational sense to drive the rack 52 downwardly by way of the spur gear 60. Thus, the placement member 50 is lowered within the inner chamber 30. When the bottom of the spline collar 56 reaches the top of the worm gear 82, the splines of these two elements may be meshed. The second crank handle 90 may be turned to rotate the worm gear as needed to align the splines of the collar 56 with the spaces between the splines of the worm gear. Then, the placement member 50 may continue to be lowered without rotation, by operation of the first handle 76 as the spline collar 56 slides along within the worm gear 82.

As the placement member 50 continues to be lowered, the collet fingers 108 pass down within the interior of the drive screw 10a. The rotary drive dogs 106 of the torque head 54 may be made to mesh with the dogs 110 of the drive screw. Again, the second crank handle 90 may be rotated as needed to align the dogs of one element with the spaces between dogs of the other. When this is accomplished, continued operation of the first crank handle 76 lowers the placement member 54 until the collet finger latches 108a snap under the shoulder 112 of the drive screw 10a. Such action by the latches 108a is caused by the bias of the collet fingers 108 to moved radially outwardly. The inner surface of the screw drive 10a is beveled, extending from the top of the dogs 106 to the edge of the shoulder 112. The outer surface of the latches 108a are also beveled. Thus, as the collet fingers 108 are moving downwardly within the drive screw 10a, they are first urged inwardly while the latches 108a move easily over the beveled surface leading to the shoulder 112, then catch under that shoulder.

With the placement member 50 thus connected to the coupon holder 10, the second handle 90 is operated to cause the torque head 54, joined to the worm gear 82 by way of the spline collar 56, to rotate in a left-hand sense relative to the pipe P. The meshing of the dogs 106 and 110 effects an application of torque on the drive screw 10a. Thus, the drive screw is turned in the nipple threads 18 to raise the drive screw relative to the nipple 12. As the drive screw 10a is initially raised in this manner, it lifts off of the seal section 10b to achieve the configuration shown in FIG. 5, wherein the pressure equalization port 136 is open for pressure communication through the drive screw. Once the shoulder 116 contacts the head of the shoulder bolt 114, continued rotation of the drive screw by way of the placement member 50 results in the drive screw raising the seal section 10b. The metal-to-metal seal at the shoulders 12b and 120 is broken. Then, the seal between the packing 122 and the inner nipple surface 12c is slowly disengaged as the crank handle 90 is continued to be turned.

As the seal section 10b is raised, the plunger 140 rides out of the nipple detent 12d and along the surface 12c, compressing the spring 142.

Once the primary seal between the packing 122 and the surface 12c is broken, the fluid pressure within the pipe P is communicated throughout the interior of the extractor tool 24. The open pressure equalization port 136 facilitates the communication of pressure beyond the holder 10 into the extractor tool. With the two bleed valves 32 and 94 closed, the pressure is contained within the extractor tool by means of various seals described hereinbefore.

The ratio between the pitch of the helical gear 86 and the pitch of the threads 18 and 118 is such that many turns of the second crank handle 90 are required to advance the seal section 12c. Thus, the seal between the coupon holder 10 and the landing nipple 12 is opened slowly to allow the large pressure differential across that seal to decrease to zero at a relatively slow rate. Consequently, the holder 10, and even the extractor tool itself, is prevented from being blown out by the sudden exposure of the high pressure within the pipe P to atmospheric pressure. Furthermore, the aforementioned pitch ratio results in a large mechanical advantage in the handle 90 to not only break the sealing of the holder 10 to the landing nipple 12, but also to resist unintended upward propulsion of the holder and placement member 50.

As the second crank handle 90 is operated to raise the drive screw 10a, and eventually also the rest of the holder 10, lifting of the placement member 50 forces the rack 52 upwardly causing the first crank handle 76 to rotate. Eventually the threads 118 of the drive screw 10a are disengaged from the threads 12a of the landing nipple 12. The spline collar 56 extends downwardly along the placement member 50 a sufficient distance to insure that the placement member and the attached drive screw 10a may be rotated to so disengage the later from the landing nipple threads 12a. Once this has occurred, the placement member 50 and the holder 10 may be more rapidly raised by operation of the first crank handle 76, without rotation of the worm gear 82. Disengagement of the spline collar 56 from the worm gear 82 occurs when the placement member is moved a short distance above the position required to just disengage the drive screw threads 118 from the landing nipple threads 12a.

When the placement member 50 and the holder 10 are raised, by operation of the first crank handle 76, above the ball valve 40, the ball valve is closed, by operation of the valve handle 100, to seal off the inner chamber 30 from the pipe P, and the configuration illustrated in FIGS. 4A and 4B is achieved. The bleed valve 94 is opened slowly to equalize the pressure between the chamber 30 and the surrounding atmosphere. Completion of such pressure equalization is indicated by the pressure gauge 92.

The nut 36 is then disengaged from the ball valve housing 38. The housing 28, the worm gear retainer 34 and the nut 36 are removed from the ball valve, exposing the inner chamber 30. The first crank handle 76 may be rotated to move the placement member 50 to expose the holder 10. The coupon (not shown) on the lower end of the holder section 10c may then be replaced. If desired, the placement member 50 may be advanced to expose the entire coupon holder 10, which may then be removed from the collet fingers 108 by a sharp pull. In this way, the coupon holder itself may be replaced, with the new holder being pushed onto the collet fingers 108.

With the new coupon (not shown) secured to the bottom of the holder section 10c (and the coupon holder replaced on the torque head 54 if necessary), the first crank handle 76 is again operated to retract the placement member 50 and the holder so that the coupon does not extend beyond the worm gear retainer 34. The extractor tool housing 28 is then positioned over the ball valve 40 and the nut 36 engages and is tightened on the threads of the valve housing. Thus, the configuration illustrated in FIGS. 4A and 4B is regained with a new coupon (not shown), and possibly a new coupon holder.

At this point a pressure differential exists across the ball valve 40, the pressure within the inner chamber 30 being atmospheric. With the bleed valves 32 and 94 closed, the ball valve element 96 is slowly turned to break the seal between that element and the packing 98. The pressure differential across the valve element 96 is thus gradually diminished by a slow, controlled leak. As the pressure builds up above the ball valve 40, as reflected by the pressure gauge 92, the valve element 96 may continue to be turned until the passage therethrough is aligned with the inner chamber 30. The placement member 50 may then be lowered to position and anchor the landing nipple 12.

The first crank handle 76 may be operated to lower the placement member 50 until the drive screw threads 118 contact the landing nipple threads 12a. Then, the torque head 54 must be rotated by means of the second crank handle 90 to screw the drive screw 10a further along the landing nipple 12. However, the method of imparting rotational and translational motions to the placement member 50 separately by way of two external handles according to the present invention allows the holder 10 to engage the landing nipple at 12 without the possibility of the drive screw threads 118 and/or the landing nipple threads 12a being damaged by an initial hard and abrupt contact. Once the placement member 50 has been lowered so that the spline collar 56 has reached the top of the worm gear 82, and the two spline elements 56 and 82 have been meshed with the aid of a slight rotation of the second crank handle 90, if necessary, the placement member may be rotated as it is further advanced toward the pipe P. Thus, while the first crank handle 76 is operated to provide the necessary translational motion, the second crank handle 90 is turned in the direction that would advance the drive screw 10a along the threads 12a of the landing nipple if such threaded engagement had already occurred. With the second crank handle 90 being continually turned as the placement member 50 is slowly lowered by rotation of the first crank handle 76, the drive screw 10a will be rotating when its threads 118 first contact the landing nipple threads 12a. Thus, as soon as such contact is made, the threads 118 and 12a mesh and the incidental rotation of the drive screw causes that element, and the attached placement member 50, to be virtually immediately drawn downwardly. This downward pull by the holder 10 is noticeable on the part of the operator turning the first crank handle 76 because the rack 52 will apply torque to the spur gear 60. Further advancement of the drive screw 10a may be effected solely by operation of the second crank handle 90. Thus, not only is the operator signaled when the drive screw threads 118 engage the landing nipple threads 12a, and thereby informed that rotation of the drive screw is now required, but such contact between the threads 118 and 12a may be effected without damage thereto.

Continued rotation of the lower crank handle 90 causes further rotation of the drive screw 10a with attendant advancement of the placement member 50 and the holder 10 downwardly relative to the landing nipple 12.

Prior to the seal section 10b passing within the inner nipple surface 12c, there is no continued source of frictional drag between the seal section and the nipple 12. Consequently, the spring biased plunger 134 may exert sufficient force to cause the seal section 10b to be displaced away from the drive screw 10a to the extent permitted by the shoulder bolt 114, as shown in FIG. 4A.

With the drive screw rotating in threaded engagement with the landing nipple 12, the seal section 10b may experience frictional drag, caused by the nipple surface 12c, resisting rotation of the seal section. This is particularly true with the spring biased plunger 140 pressing against the surface 12c. However, if rotation of the drive screw 10a occurs relative to the seal section 10b in such case, the spring biased plunger 130 will eventually engage the detent 134 to impart sufficient torque to the seal section to overcome the frictional forces. Thus, the seal section 10b is made to rotate about its longitudinal axis while passing downwardly within the surface 12c. As the seal section 10b thus rotates, the holder section 10c, with coupon attached, rotates within the pipe P.

Eventually, the seal section 10b is lowered within the landing nipple 12 to the point where the spring biased plunger 140 engages the detent 12d in the interior of the landing nipple as illustrated in FIG. 5. The force with which the plunger 140 is maintained in the detent is such that continued rotation of the drive screw 82 causes the plunger 130 to ride out of the detent 134, compressing the spring 126. The drive screw 10a then rotates and advances along the landing nipple threads 12a while the seal section 10b and the holder section 10c remain stationary.

The clutch 124 thus ensures that the seal section 10b is rotated relative to the nipple 12 until the spring biased plunger 140 engages the detent 12d to lock the coupon oriented within the pipe P in the direction desired. Once this orientation of the holder section 10c is assured, there is no further need for rotation of the seal section 10b, and the clutch at 124 is rendered inoperative by the disengagement of the plunger 130 from the detent 134 with continued rotation of the drive screw 10a.

It will be appreciated from the drawings, and previous discussion, that just prior to the engagement of the plunger 140 with the detent 12d the primary seal between the packing 122 and the surface 12c is closed. By the time the plunger 140 engages the detent 12d, the sealing surface of the packing 122 is in total engagement with the nipple surface 12c and this primary sealing is complete. However, the metal-to-metal seal between the surfaces 120 and 12b of the seal section and landing nipple, respectively, is not closed until the seal section is forced downwardly against the landing nipple without further rotation. Such force is provided after the drive screw is further rotated to advance and close the gap between its bottom surface and the top of the seal section 10b. Then, tightening the drive screw 10a in the nipple threads 12a presses the drive screw down against the seal section 10b, causing the surface 120 to press against the nipple surface 12b in sealing engagement. In this way, the metal-to-metal seal between the holder 10 and the nipple 12 is set without relative rotation between the sealing surfaces 12b and 120. Sufficient pressure is applied, by way of the tightening of the drive screw in the threads 12a, to effect a high pressure fluid-tight seal between the mutually facing surfaces 12b and 120. This pressure is maintained effective due to the low pitch of the threads 12a and 118 holding the drive screw 10a in position relative to the landing nipple 12.

At this point, the entire holder at 10 is in operating configuration, and the extractor tool 24 may be disengaged and removed. With the second crank handle 90 no longer being operated, a short, sharp turn of the first crank handle 76 in the direction to raise the rack 52 will cause the collet latches 108a to ride around the shoulder 112 to release the placement member 50 from the holder 10. The upwardly facing surfaces of the collet latches 108a are tapered upwardly and inwardly as shown in the drawings to facilitate this abrupt movement around the shoulder 112, although such tapering is not sufficient to disengage the collet fingers 108 from the drive screw 10a when the holder 10 is being lifted, free of threaded engagement with the landing nipple 12.

The first crank handle 76 is continually rotated to draw the placement member 50 upwardly so that the collet fingers 108 clear the top of the landing nipple 12. The bleed valve 94 may then be opened to slowly leak the high pressure within the extractor tool 24 to the atmosphere. The double sealing by the packing 122 and the metal-to-metal seal of the surfaces 12b and 120 prevents the higher pressure within the pipe P from communicating upwardly beyond the seal section 10b. When the pressure gauge 92 indicates that there is no pressure differential between the inner chamber 30 and the surrounding atmosphere the floating nut 26 may be rotated and disengaged from the external threads 18 of the landing nipple to remove the extractor tool therefrom. Again, the nut 42 may be loosened, if necessary, to facilitate rotation of the floating nut 26.

With the extractor tool at 24 removed the cap 16 may be replaced to cover the open end of the landing nipple. Tightening the cap 16 on the external threads 18 of the landing nipple 12 again provides a fluid-tight seal therebetween as a safety measure. The pressure within the cap 16 above the seal section 10b is then atmospheric.

Figure 8:
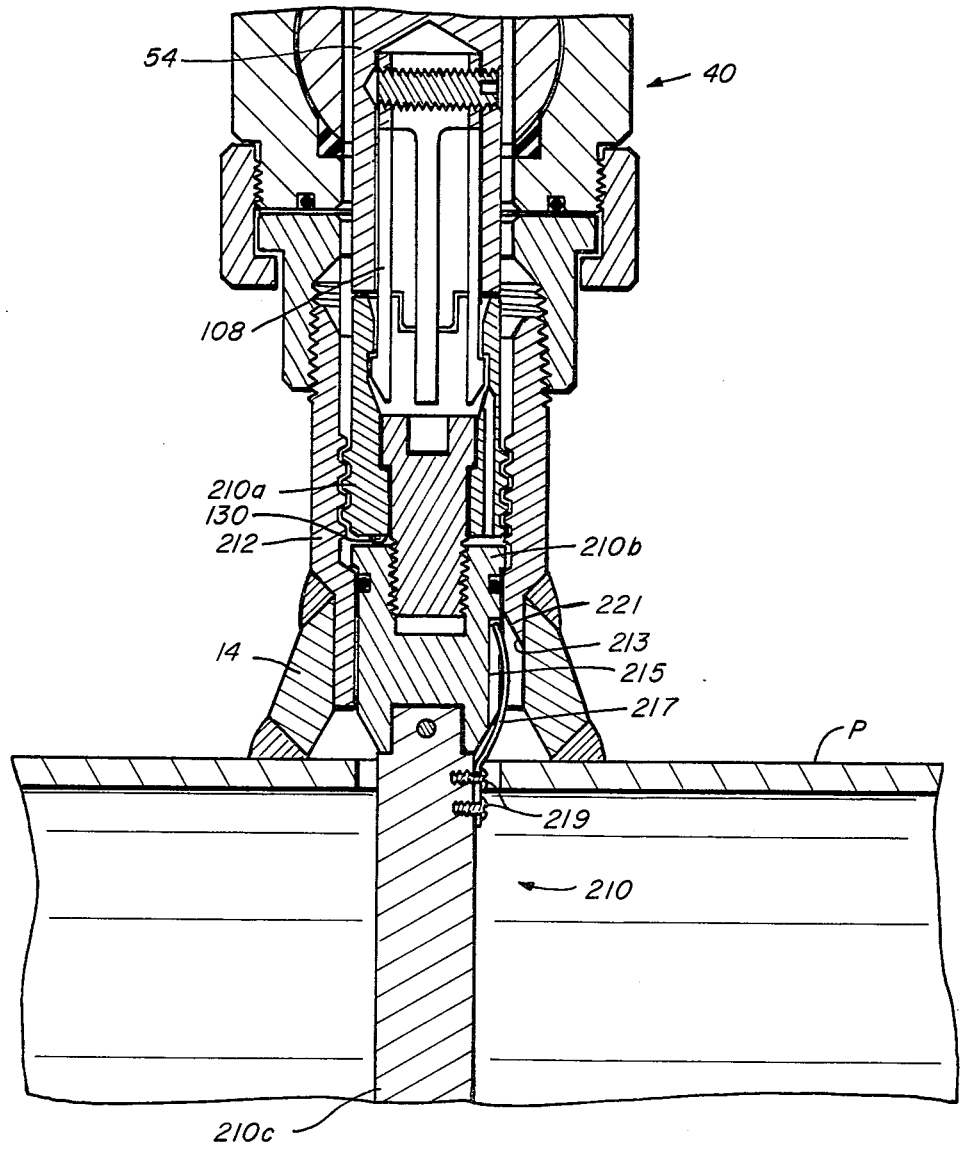
FIG. 8 is a view similar to that of FIG. 6, but showing another embodiment of the coupon holder.

In FIG. 8, another holder at 210, according to the present invention, is shown positioned within a variation of a landing nipple 212, and engaged with the torque head 54 of the extractor tool as previously described. The landing nipple 212 includes a longitudinally extending detent or groove 213. The holder 210 includes a drive screw 210a similar to the drive screw 10a, a seal section 210b and a holder section 210c. The seal section 210b features a longitudinally extending recess 215 which receives a leaf spring 217 whose end is fixed to the holder section 210c by screws 219. In all other respects, the construction of the holder 210 is like that of the holder 10, and the construction of the landing nipple 212 is like that of the landing nipple 12.

As the holder 210 is being inserted into the landing nipple 212, and the drive screw 210a is being rotated in engagement with the landing nipple internal threads, the leaf spring 217 is held within the recess 215 by the interior surface of the landing nipple. However, once the seal section 210b has been lowered sufficiently and oriented to allow the leaf spring 217 to expand into the landing nipple detent 213, engagement of the leaf spring within the detent prevents further rotation by the seal section, thereby ensuring a specific alignment of the seal section and the holder section 210c. As shown in FIG. 8, the upper limit of the detent 213 is defined by the inwardly sloping surface 221. As the seal section 210b is raised in the process of removing the holder 210 from the landing nipple 212, the leaf spring 217 engages the surface 221, and is forced thereby into the recess 215.

While the extractor and holder according to the present invention have been described in terms of positioning a coupon within a high pressure pipeline, the present invention may be used to provide general access to the interior of such a pipeline or other enclosure. Further, by appropriate selection of construction materials, particularly the resilient seals, the present invention may be utilized for access to the interior of a container of pressurized fluids of extreme temperature, either high or low. In such case, the controlled venting of a portion of the fluid to the atmosphere prior to removing the extractor tool having from the ball valve avoids a possible burst or spray of fluid, of extreme temperature, to the surroundings.

The extractor tool of the present invention may be operated without the need of the operator being positioned at any time directly above the extractor housing. Thus, the operator need not be in line over the landing nipple and pipeline tap in the event a blowout does occur. The bleed valve 32 positioned at the end of the housing 28a may serve as a backup to the side-mounted valve 94 for bleeding pressure to the atmosphere with the latter valve being normally used for that purpose to avoid having the operator extend a hand in the vicinity of the end of the tool 24.

Where toxic, or other possible polluting material is contained within the pipeline, a feed line may be connected to the bleed valve 90 (and 32) to collect the vented fluid rather than allow it to leak to the atmosphere.

It will be appreciated from the construction described herein that the holder of the present invention may be mounted in a landing nipple oriented in any direction, and that the extractor tool may also be operated in any orientation.

The construction of the holder to permit limited translational movement between the seal section and the drive screw allows the seal section to be locked into a desired orientation followed by the drive screw being tightened without further rotation of the seal section. Thus, not only are the seal and holder sections oriented as desired before the final positioning of the holder in general, but the tightening of the holder in the landing nipple without rotation of the seal section permits the use of a metal-to-metal seal. Further, during the retrieval process, lifting the drive screw off of the seal section allows the pressure equalization port to be opened to speed the equalization of pressure across the holder once the seals to the nipple begin opening.

The capability of imparting either translational or rotational movement to the placement member independently, one without the other, permits use of the drive dog and collet latch engagement between the placement member and the holder. Thus, the torque head may be disengaged from the holder without rotation that might disturb the tightened anchoring of the drive screw to the nipple threads. Further, pure translational movement may be used to retract the placement member rapidly, for example, while rotational movement, accompanied by a large mechanical advantage but slow advancement of the placement member is used to engage or disengage the drive screw with the nipple.

It will be appreciated that the alignment of the spline collar with the worm gear, as well as the alignment of the rotary drive dogs, may be felt by the operator as the two crank handles are operated at the same time. Where no rotational adjustment is needed, in either case, the operator is also aware of the meshing as the translational movement of the placement member proceeds. Also, as noted hereinbefore, with rotation of the placement member as the drive screw is being moved toward the landing nipple, engagement of the drive screw threads with those of the nipple results in a tug on the placement member transmitted to the first crank handle, notifying the operator that the drive screw has threadedly engaged the nipple.

The foregoing disclosure and description of the invention is illustrative and explanatory thereof, and various changes in the method steps as well as in the details of the illustrated apparatus may be made within the scope of the appended claims without departing from the spirit of the invention.

We claim:

1. Apparatus for use with containers of fluid under pressure comprising:
   (a) landing means generally circumscribing a passage to the interior of such a container;
   (b) holder means for selective mounting on said landing means;
   (c) seal means for sealing said holder means to said landing means;
   (d) anchor means for anchoring said holder means to said landing means;
   (e) said holder means including a drive screw, and said anchor means including threads on said drive screw and threads on said landing means whereby said drive screw may be threadedly engaged with said landing means;
   (f) orientation means for automatically retaining at least a portion of said holder means in a preselected rotational orientation relative to said landing means when said holder means is sealed and anchored to said landing means;
   (g) manipulating tool means for selectively maneuvering said holder means, including:
      (i) placement means for selectively engaging said holder means;
      (ii) first means for selectively imparting translational motion to said placement means; and
      (iii) second means for selectively imparting rotational motion to said placement means.

2. Apparatus as defined in claim 1 wherein:
   (a) said holder means further includes a seal section connected to said drive screw, and said seal means includes cooperating seal elements as part of said seal section and said landing means;
   (b) said orientation means includes engagement means, as part of said holder means, and recess means, as part of said landing means, for receiving said engagement means to thereby prevent rotation of said seal section; and
   (c) said holder means further includes means for permitting relative rotation between said drive screw and said seal section.

3. Apparatus as defined in claim 2 wherein said connection of said seal section to said drive screw includes means to resist relative translational movement therebetween.

4. Apparatus as defined in claim 3 wherein said drive screw includes bypass port means for communicating fluid pressure through said drive screw.

5. Apparatus as defined in claim 2 wherein:
   (a) said placement means includes latch means and first torque communicating means;
   (b) said drive screw includes shoulder means and second torque communicating means; and
   (c) said placement means engages said holder means by said latch means gripping said shoulder means and said first torque communicating means engaging said second torque communicating means such that rotation of said placement means imparts torque to said drive screw.

6. Apparatus as defined in claim 5 or, in the alternative, as defined in claim 1 wherein:
   (a) said tool means may be sealingly engaged to said landing means;
   (b) said tool means includes valve means; and
   (c) said tool means further includes housing means which may be disengaged from said valve means.

7. Apparatus as defined in claim 2 wherein said seal means further includes a first set of cooperating seal elements as parts of said seal section and said landing means to effect a first seal therebetween, and a second set of cooperating seal elements as parts of said seal section and said landing means to effect a second seal therebetween.

8. Apparatus as defined in claim 7 or, in the alternative, as defined in claim 6 wherein said seal elements include a metal seal element as part of said seal section and a metal seal element as part of said landing means, said two metal seal elements effecting a fluid-tight seal when held in mutual contact.

9. Apparatus as defined in claim 2 or, in the alternative, as defined in claim 1 wherein said placement means may transmit translational and rotational movement to at least a part of said holder means by said engagement therebetween.

10. Apparatus as defined in claim 2 wherein said engagement means includes leaf spring means mounted on said holder means.

11. Apparatus as defined in claim 2 wherein said engagement means includes plunger means biased by spring means.

12. Apparatus as defined in claim 2 further comprising clutch means, including biased means carried by one of said seal section or said drive screw, engageable with recess means as part of the other of said seal section or said drive screw for imparting torque between said drive screw and said seal section.

13. Apparatus for use with containers of fluid under pressure, and including landing means generally circumscribing a passage to the interior of such a container, comprising:
   (a) holder means for selective mounting on said landing means;
   (b) seal means, including a metal seal element as part of said holder means and a metal seal element as part of said landing means whereby said holder means may be fluid-sealed to said landing means by said two cooperating metal seal elements closing in fluid-tight sealing engagement without relative rotational motion therebetween;

(c) anchor means for anchoring said holder means to said landing means by threaded engagement; and (d) orientation means whereby at least a portion of said holder means is automatically retained in a preselected orientation relative to said landing means when said holder means is sealed and anchored to said landing means.

14. Apparatus as defined in claim 13 wherein:

(a) said anchor means includes a drive screw as part of said holder means;

(b) said holder means further comprises a seal section including at least one such seal element;

(c) said seal section is connected to said drive screw by a coupling permitting limited relative translational movement between said drive screw and said seal section;

(d) said holder means further comprises clutch means operable for linking said seal section and said drive screw against relative rotational motion therebetween; and (e) said orientation means operates to lock said seal section against rotational motion relative to said landing means when said seal section has been positioned within said landing means in a preselected orientation relative to said landing means, whereupon said clutch means is overriden so that said drive screw is rotatable relative to said seal section.

15. Apparatus as defined in claim 14 wherein said seal means further comprise
packing means as part of one of said landing means or said seal section, and seat means as part of the other of said landing means or said seal section.

16. Apparatus for use with containers of fluid under pressure, and including landing means, comprising tool means for selectively manipulating equipment relative to said landing means, wherein said tool means further comprises:

(a) coupling means for selectively coupling said tool means to said landing means in fluid-tight engagement;

(b) housing means providing an inner chamber;

(c) placement means for selectively engaging such equipment, and movable within said chamber;

(d) first gear means for selectively imparting translational motion to said placement means; and (e) second gear means for selectively imparting rotational motion to said placement means.

17. Apparatus as defined in claim 16 further comprising valve means, as part of said tool means, for interposing between said housing means and said coupling means for providing a fluid-tight closure, and such that said valve means may be closed and said housing means selectively disengaged from said valve means to thereby generally expose said chamber.

18. Apparatus as defined in claim 16 further comprising bleed valve means communicating with said chamber whereby fluid pressure may be vented through said housing.

19. Apparatus as defined in claim 16 wherein said placement means may selectively engage such equipment to impart translational or rotational movement thereto.

20. Apparatus as defined in claim 16 wherein said first gear means includes spur gear means for engaging rack means, as part of said placement means, whereby rotation of said spur gear means may impart translational motion to said placement means.

21. Apparatus as defined in claim 20 or, in the alternative, as defined in claim 18 wherein said second gear means includes worm gear means for engaging with said placement means for imparting rotational motion thereto, and helical gear means engaged with said worm gear means, whereby, with said worm gear means so engaged with said placement means, rotation of said helical gear means imparts rotational motion to said placement means.

22. A method of manipulating equipment for use on a container of fluid equipped with a landing fitting for receiving said equipment by threaded connection thereto comprising the following steps:

(a) mounting a manipulating tool on said fitting wherein said tool includes a housing and valve between said housing and said fitting;

(b) passing a placement device through said valve, in open configuration, to insert or retrieve such equipment relative to said fitting;

(c) rotating said placement device to engage or disengage said threaded connection between said equipment and said fitting; and (d) closing said valve to seal the interior of said fitting relative to the environment to permit the location of such equipment on said placement device outside of said fitting in anticipation of such insertion, or as a result of said retrieval.

23. A method of removing equipment from a fitting on a container of fluid, whereby said equipment communicates with the interior of said container, comprising the following steps:

(a) mounting a manipulating tool on said fitting wherein said tool includes a valve, a housing connected to said valve opposite the fitting, and a placement device extendable through said valve;

(b) connecting said placement means to said equipment;

(c) disengaging said equipment from said fitting by imparting torque to said placement means to rotate said equipment relative to said fitting;

(d) retracting said placement means, with said equipment attached, through said valve at least partially into said housing;

(e) closing said valve; and (f) disengaging said housing from said valve to expose said equipment.

24. A method as defined in claim 23 further comprising the additional step of opening a bleed valve to equalize pressure within said housing and the environment after closing said first valve but before disengaging said housing from said first valve.

25. A method as defined in claim 24 or, in the alternative, as defined in claim 23 wherein the step of retracting said placement means is carried out generally without rotation of said placement means.

26. A method of mounting equipment on a fitting on a container of fluid, whereby said equipment may communicate with the interior of said container, comprising the following steps:

(a) providing a manipulating tool including a valve, a housing connectable to said valve, and a placement device extendable through said valve, with said valve mounted on said fitting and in a closed configuration;

(b) with said placement device engaging said equipment, and retracted at least in part within said housing, mounting said housing on said valve opposite said fitting;

(c) opening said valve;

(d) extending said placement device through said valve to position said equipment adjacent said fitting;

(e) applying torque to said placement device to effect engagement of said equipment with said fitting, automatically orienting and locking at least a portion of said equipment in a predetermined rotational orientation relative to said fitting; and (f) disconnecting said placement device from said equipment.

27. A method as defined in claim 26 further comprising the additional step of disconnecting said valve from said fitting after said placement device is disconnected from said equipment.

28. A method as defined in claim 27, or, in the alternative, as defined in claim 26 further comprising the additional step of venting fluid from within said tool after said equipment is so engaged with said fitting.

29. A method as defined in claim 28 wherein the step of engaging said equipment with said fitting includes sealing said equipment to said fitting and anchoring said equipment to said fitting.

30. A method as defined in claim 29 wherein said sealing of said equipment to said fitting includes closing two fluid-tight seals between said equipment and said fitting.

31. A method as defined in claim 29 wherein said sealing of said equipment includes closing a metal-to-metal fluid-tight seal between said equipment and said fitting.

32. A method as defined in claim 29 wherein the step of engaging said equipment with said fitting includes rotating at least a portion of said equipment to anchor said equipment to said fitting, and moving at least a portion of said equipment translationally without rotation thereof to seal said equipment to said fitting.

33. A method as defined in claim 26 wherein the step of engaging said equipment with said fitting includes sealing said equipment to said fitting and anchoring said equipment to said fitting.

34. A method as defined in claim 33 wherein said sealing of said equipment to said fitting includes closing two fluid-tight seals between said equipment and said fitting.

35. A method as defined in claim 33 wherein said sealing of said equipment includes closing a metal-to-metal fluid-tight seal between said equipment and said fitting.

36. A method as defined in claim 33 wherein the step of engaging said equipment with said fitting includes rotating at least a portion of said equipment to anchor said equipment to said fitting, and moving at least a portion of said equipment translationally without rotation thereof to seal said equipment to said fitting.

37. Apparatus for mounting equipment for communication with the interior of containers of fluid under pressure comprising:

(a) landing means for connection to such a container to generally circumscribe a passage communicating with the interior of said container;

(b) holder means on which said equipment may be mounted and which may be received by said landing means; and (c) cooperating locking means as part of said holder means and as part of said landing means, and including spring biased engagement means and recess means, whereby at least a portion of said holder means is automatically locked in a predetermined rotational orientation relative to said landing means by said engagement means engaging said recess means when said holder means is mounted on said landing means.

38. Apparatus for mounting equipment for communication with the interior of containers of fluid under pressure comprising:

(a) landing means for connection to such a container to generally circumscribe a passage communicating with the interior of said container;

(b) holder means on which said equipment may be mounted, and which may be received by said landing means;

(c) a seal section, as part of said holder means, for fluid-sealing said holder to said landing means when said holder is mounted on said landing means;

(d) an anchor section, as part of said holder means, for anchoring said holder means to said landing means when said holder means is mounted on said landing means;

(e) connection means joining said seal section to said anchor section, and permitting limited relative translational motion therebetween; and (f) clutch means as part of said holder means for imparting torque between said anchor section and said seal section.

39. Apparatus as defined in claim 38 wherein:

(a) said holder section is so anchored to said landing means by said anchor section being rotated and thereby threadedly engaging said landing means;

(b) said clutch means causes said seal section to rotate with said anchor section during at least a part of said rotation by said anchor section to so threadedly engage said landing means; and (c) said holder means further comprises lock means whereby said seal section is automatically locked against rotational motion relative to said landing means when said seal section is positioned within said landing means in a predetermined orientation relative to said landing means.

40. Apparatus as defined in claim 39 wherein said lock means includes spring biased engagement means for engaging recess means, as part of said landing means, to so lock said seal section.

41. Apparatus as defined in claim 39 wherein, with said seal section locked against rotation relative to said landing means by said lock means, said connection means between said anchor section and said seal section permits said anchor section to be rotated to further advance said anchor section along said landing means to close a seal between said seal section and said landing means.

42. Apparatus as defined in claim 41 wherein said seal, between said seal section and said landing means, so closed by further advancement of said anchor section comprises a metal-to-metal seal.

43. Apparatus for mounting or removing equipment for use on containers of fluid under pressure, such a container being equipped with landing means for receiving such equipment and generally circumscribing a passage for communication with the interior of said container, comprising:

(a) valve means for coupling to said landing means for selectively sealing said landing means closed;

(b) housing means, selectively connectable to said valve means in fluid-tight sealing engagement whereby, with said valve means open, the interior of said housing means may communicate with the interior of said landing means;

(c) elongate placement means for carrying such equipment and for selectively inserting said equipment within, or removing said equipment from, said landing means;

(d) first gear means for imparting translational motion to said placement means relative to said housing means;

(e) second gear means for imparting rotational motion to said placement means relative to said housing means; and (f) engagement means, as part of said placement means, for selectively connecting said placement means to said equipment, and including latch means for connecting to said equipment for imparting translational motion thereto, and rotary drive means for imparting rotational motion to said equipment 44. Apparatus as defined in claim 43 further comprising bleed valve means whereby fluid pressure may be vented from within said housing means.

45. Apparatus as defined in claim 43 wherein said placement means includes rack means, and said first gear means includes spur gear means for engaging said rack means whereby rotation of said spur gear means may impart translational motion to said placement means.

46. Apparatus as defined in claim 45 or, in the alternative, as defined in claim 43 wherein:
 (a) said placement means includes first spline means;
 (b) said second gear means includes second spline means, worm gear means, and helical gear means;
 (c) said second spline means and said worm gear means are mutually fixed against relative rotational motion therebetween;
 (d) said helical gear means engages said worm gear means so that rotation of said helical gear means causes said worm gear means and said second spline means to rotate; and
 (e) said first spline means is connectable to said second spline means so that rotation of said second spline means may cause rotation of said placement means.

47. Apparatus as defined in claim 46 wherein said first spline means so connects with said second spline means when said placement means is positioned such that said equipment, so connected to said placement means, is adjacent said landing means.

48. Apparatus for use with containers of fluid under pressure comprising:
 (a) holder means;
 (b) valve means for selective coupling to such a container;
 (c) housing means for selective mounting on said valve means;
 (d) placement means for selectively engaging said holder means;
 (e) gear means for selectively applying forces to move said placement means translationally or rotationally relative to said housing means whereby such forces to effect such translational and rotational movements of said placement means may be so applied generally independently of each other;
 (f) cooperating engagement means as parts of said placement means and said holder means whereby said placement means may be so engaged with said holder means to impart translational or rotational motion thereto;
 (g) said placement means including rack means, and said gear means including spur gear means for engaging said rack means whereby rotation of said spur gear means may apply force to said rack means to so move said placement means translationally;
 (h) said placement means further including first spline means, and said gear means further including second spline means, worm gear means fixed against rotational motion relative to said second spline means, and helical gear means for engaging said worm gear means so that rotation of said helical gear means causes said worm gear means and said second spline means to rotate; and
 (i) said first and second spline means are connectable so that rotation of said second spline means may cause rotation of said placement means.

49. Apparatus as defined in claim 48 further comprising landing means, connected to said container, for receiving said valve means whereby said valve means may be so selectively coupled to said container in sealing engagement, and for receiving said holder means whereby said holder means may be held in sealing and anchoring engagement relative to said landing means.

50. Apparatus as defined in claim 49 further comprising orienting means as parts of said holder means and said landing means whereby said orienting means of said holder means and said landing means cooperate so that at least a portion of said holder means is automatically oriented and locked in a predetermined direction relative to said landing means when said holder means is so held in sealing and anchoring engagement by said landing means.

51. Apparatus as defined in claim 50 wherein said sealing engagement between said holder means and said landing means is effected by a metal-to-metal seal therebetween.

52. Apparatus as defined in claim 49 wherein said sealing engagement between said holder means and said landing means is effected by a metal-to-metal seal therebetween.

53. Apparatus as defined in claim 49 wherein said holder means comprises:
 (a) an anchor section for anchoring said holder means to said landing means by threaded engagement therebetween;
 (b) a seal section for sealingly engaging said holder means to said landing means; and
 (c) connection means whereby said seal section is joined to said anchor section, permitting limited relative translational motion therebetween, and including clutch means for transmitting torque between said anchor section and said seal section.

54. Apparatus as defined in claim 48 wherein said holder means comprises:
 (a) an anchor section for selectively anchoring said holder means relative to said container;
 (b) a seal section for selectively sealing said holder means relative to said container; and
 (c) connection means whereby said seal section is joined to said anchor section, permitting limited relative translational motion therebetween, and including clutch means for transmitting torque between said anchor section and said seal section.

55. Apparatus as defined in claim 54 further comprising cooperating metal seal elements for so selectively sealing said holder means relative to said container.

56. Apparatus as defined in claim 48 further comprising orienting means whereby at least a portion of said holder means may be automatically oriented and locked in a predetermined orientation relative to said container.

57. Apparatus as defined in claim 48 further comprising cooperating metal seal elements whereby said holder means may be selectively sealed relative to said container.

58. Apparatus for use with containers of fluid under pressure, and including landing means generally circumscribing a passage to the interior of such a container, comprising:
  (a) holder means for selective mounting on said landing means;
  (b) seal means, including cooperating seal elements as parts of said holder means and said landing means whereby said holder means may be fluid-sealed to said landing means;
  (c) anchor means for anchoring said holder means to said landing means by threaded engagement and including a drive screw as part of said holder means;
  (d) a seal section, as part of said holder means, including at least one such seal element and connected to said drive screw by a coupling permitting limited relative translational movement between said drive screw and said seal section;
  (e) said holder means further comprising clutch means operable for linking said seal section and said drive screw against relative rotational motion therebetween; and
  (f) orientation means for locking said seal section against rotational motion relative to said landing means when said seal section has been positioned within said landing means in a preselected orientation relative to said landing means, whereupon said clutch means is overriden so that said drive screw is rotatable relative to said seal section, and whereby said seal section is automatically retained in said preselected orientation relative to said landing means when said holder means is sealed and anchored to said landing means.

59. Apparatus as defined in claim 58 wherein said cooperating seal elements include packing means as part of one of said landing means or said seal section, and seat means as part of the other of said landing means or said seal section.

* * * * *